United States Patent [19]

Spector

[11] 3,976,763

[45] Aug. 24, 1976

[54] CHLORPROMAZINE ASSAY

[75] Inventor: Sidney Spector, Livingston, N.J.

[73] Assignee: Hoffmann-La Roche Inc., Nutley, N.J.

[22] Filed: Apr. 30, 1975

[21] Appl. No.: 573,227

[52] U.S. Cl. .............................. 424/1.5; 23/230 B; 260/112 R; 424/12; 424/85
[51] Int. Cl.² .................. G01N 33/00; A61K 39/00
[58] Field of Search .................... 424/1, 1.5, 12, 85; 260/112 R; 23/230 B

[56] References Cited
OTHER PUBLICATIONS

Frey et al., Zentralblatt fuer Pharmazie, Pharmakotherapie und Labratorumsdiagnostic, vol. 113, No. 12, 1974, pp. 1279–1284.
Ekren et al., Nuclear Science Abstracts, vol. 28, No. 3, Aug. 15, 1973, abstract No. 6007, p. 570.
Glebov et al., Chemical Abstracts, vol. 71, No. 11, Sept. 15, 1969, abstract No. 47947v, p. 205.
Anisimor, Chemical Abstracts, vol. 68, No. 17, Apr. 22, 1968, abstract No. 76645p, p. 7387.

*Primary Examiner*—Benjamin R. Padgett
*Assistant Examiner*—Christine M. Nucker
*Attorney, Agent, or Firm*—Samuel L. Welt; George M. Gould

[57] ABSTRACT

A sensitive radioimmunoassay for chlorpromazine is described. To prepare the chlorpromazine selective antiserum, an antigen is made comprising chlorpromazine covalently bonded to an immunogenic carrier material through a diazo containing linking group and the antigen is injected into a suitable host mammal to elicit the desired antiserum. A preferred linking group is diazophenylcarbonyl while bovine serum albumin is a preferred immunogenic carrier material.

9 Claims, No Drawings

CHLORPROMAZINE ASSAY

BACKGROUND OF THE INVENTION

Chlorpromazine and its analogs are widely used in the therapy of psychiatric patients and also in experimental pharmacologic studies. Available methods for the determination of chlorpromazine in plasma are somewhat laborious in that they require extraction followed by fluorescent labeling using dansyl chloride, thin layer chromatography and spectroflorometry (Forrest et al., Agressologie 12, 127 (1970); Kaul et al., Nature 226, 372 (1970)); gas-liquid chromatography (Curry, Anal. Chem. 40, 1251 (1968)) or labeled derivative formation (Efron et al., Psychopharmacologia 19, 207 (1971)).

SUMMARY OF THE INVENTION

Anitserum against chlorpromaxine was produced in a mammalian subject (rabbits) immunized with chlorpromaxine hapten conjugated to bovine serum albumin by means of a diazophenylcarbonyl linking group. The antiserum is used to develop an immunoassay for chlorpromazine. As little as 10 pg of chlorpromazine can be detected with the chlorpromazine radioimmunoassay. Major metabolites such as chlorpromazine sulfoxide, $nor_1$-chlorpromazine and $nor_2$-chlorpromazine are not bound significantly by the antibody unless the concentrations are very high. Although the antibody can bind 7-hydroxychlorpromazine, 8-hydroxychlorpromazine and promazine, the concentrations required to produce a 50% inhibition of $^3$H-chlorpromazine-antibody binding are 5–10 times greater than chlorpromazine. Thus the instant assay can be used for selectively detecting chlorpromazine levels in the plasma and brain with high sensitivity.

DESCRIPTION OF THE INVENTION

The present invention relates in one aspect to a novel antigen comprising chlorpromazine coupled to an immunogenic carrier material through a diazophenylcarbonyl linking group. This antigen is conveniently prepared by conjugating diazotized p-aminobenzoic acid to chlorpromazine followed by covalently binding the free carboxyl group to available amino groups in the immunogenic carrier material to form peptide linkages. The exact point of attachment of the linking group to the chlorpromazine is not exactly known but such location is not narrowly critical to the practice of the present invention. It is believed that the diazo coupling most likely occurs on the aromatic ring at positions 3 or 7 of the chlorpromazine molecule. In such manner the important antigenic determinant groups on the chlorpromazine molecule such as the methyl group on the side chain nitrogen atom are not affected.

As used herein the term "immunogenic carrier material" is meant to include those materials which have the property of independently eliciting an immunogenic response in a host animal when injected therein and which can be coupled by covalent bonding to said chlorpromazine hapten. Suitable carrier materials include, for example, materials such as proteins; natural or synthetic polymeric compounds such as polypeptides, e.g., polylysine; polysaccharides; and the like. A particularly preferred carrier material for the practice of the present invention is protein.

The identity of the protein carrier material utilized in the preparation of the instant antigen is not narrowly critical. Examples of preferred proteins useful in the practice of this invention include the serum proteins preferably mammalian serum proteins, such as, for example, human gamma globulin, human serum albumin, rabbit serum albumin, bovine gamma globulin and bovine serum albumin. Other suitable protein products will be suggested to one skilled in the art. It is generally preferred that proteins be utilized which are foreign to the animal host in which the resulting antigen will be employed.

The first step in the preparation of the subject antigen involves conjugating diazotized p-aminobenzoic acid to chlorpromazine. The p-aminobenzoic acid may be diazotized in a manner known per se such as for example using nitrous acid which is conveniently generated by adding sodium nitrite to aqueous mineral acid, e.g., hydrochloric acid. After the diazonium salt is prepared, chlorpromazine, preferably in the form of an acid addition salt such as the hydrochloride is added in aqueous solution. After completion of the reaction, 12 to 24 hours, the pH is raised by addition of base to about 5.6 and the product hapten isolated by extraction with an organic solvent, i.e., a halogenated hydrocarbon such as methylene chloride.

Excess nitrous acid may be removed from the diazonium salt solution prior to addition of the chlorpromazine by adding a suitable agent such as ammonium sulfamate in a manner known per se. Moreover, the reaction mixture of the coupling can contain an acid acceptor such as sodium acetate if desired.

The resulting hapten can then be coupled to the immunogenic carrier material by any of the many procedures known in the art for this purpose. One particularly preferred procedure involves use of the mixed anhydride technique. Such technique employs a trilower alkyl amine, i.e., triethylamine and a lower alkyl chloroformate, i.e., iso-butyl chloroformate to form the desired reagent solution with the hapten in an aqueous cyclic ether solvent, preferably aqueous dioxane. This solution is then added to an aqueous solution of the immunogenic carrier material which may also contain some of the cyclic ether solvent.

The reaction is preferably conducted at temperatures below room temperature preferably at about 8°C. A pH of about 9 for the reaction mixture is desirable. After completion of the reaction, the antigen can be isolated by conventional procedures such as, for example, by dialysis followed by lyophilization.

The antigen of the present invention may then be utilized to induce formation of chlorpromazine specific antibodies in the serum of host animals by injecting the antigen in such host repeatedly over a period of time. The collected serum may be used per se as a chlorpromazine specific antiserum or, if desired, the antibodies therein may be further purified by precipitation with a neutral salt solution followed by dialysis and column chromatography.

Suitable host animals for preparing antiserum to chlorpromazine include mammals such as rabbits, horses, goats, guinea pigs, rats, cows, sheep, and the like. The resulting antibodies will have a multiplicity of active sites which will selectively complex with chlorpromazine, the chlorpromazine antigen of the present invention or closely related derivatives of chlorpromazine.

The formation of chlorpromazine specific antibodies in the host animals may be monitored by taking blood samples from the host animal and adding it to an amount of the hapten-protein antigen. The presence of precipitate indicates antibody activity. The antigen treatment of the animal can be continued until the antibody titre reaches a desired level of activity. For the purposes of this application the antibody titre is defined as being the maximum concentration of protein precipitated following the addition of varying known concentrations of antigens to fixed volumes of serum, e.g., 0.5 ml.

The specific antibodies of the present invention are useful as reagents in biochemical assays for the determination of the presence of chlorpromazine and closely related compounds in biological fluids. A particularly preferred assay pocedure is the immunoassay procedure such as described in U.S. Pat. No. 3,709,868. Preferred labeled chlorpormazines for use in immunoassay include the isotopically labeled chlorpromazines, particularly chlorpormazine-$H^3$, as well as chlorpromazine labeled with an electron spin resonance group. Examples of the use of various electron spin resonance labeled molecules in bioassays are to be found in U.S. Pat. Nos. 3,453,288, 3,481,952 and 3,507,876.

The radioimmunoassay method is preferred for the determination of chlorpromazine. It is a sensitive, simple and rapid procedure. Thus it is possible to determine as little as 10 pg. of chlorpormazine in plasma using 10 $\mu$l of sample without the need of extraction.

EXAMPLE 1

Preparation of Immunogen

Chlorpormazine (CPZ) was conjugated to bovine serum albumin (BSA) by initially conjugating the diazotized p-aminobenzoic acid to CPZ and then forming an amide linkage between the amine groups of the protein and the carobxyl group of benzoic acid. The exact procedure is as follows and was performed at 0–4°C.

Diazocoupling

Three hundred fifty mg. (2.4 mmol) of p-aminobenzoic acid was dissolved in 3 ml. of water and 0.7 ml. of concentrated hydrochloric acid. One ml. of water containing 2.5 mmole of sodium nitrite was added dropwise and stirred for 30 minutes. To remove the excess nitrous acid, 0.15 ml. of 1M ammonium sulfate was added slowly with constant stirring for 10 minutes. CPZ hydrochloride (2.5 mmol) was dissolved in distilled water and added gradually to the diazonium salt of p-aminobenzoic acid with continuous stirring. One ml. of water containing 2 mmol of sodium acetate was then added. Six hours later another 2 mmol of the sodium acetate was added. The pH of the solution was 1.5. The reaction was allowed to continue overnight at 4°C. with constant stirring. The solution was then adjusted to pH 5.6 with 0.5N NaOH and extracted with 30 ml. of methylene chloride. The organic layer was washed twice with water and evaporated to dryness under vacuum. The dried material had a slightly purple color. On TLC plate, Silica Gel GF, 250 micron, developed with methanol-chloroform-$NH_4OH$ (20:80:5), the compound had a Rf value of 0.27, while that of CPZ was 0.95.

Conjugation of the diazotized CPZ hapten to BSA

CPZ hapten was coupled to BSA by the mixed anhydride technique with use of isbutyl chloroformate. Triethylamine (0.05 mmol) and iso-butyl chloroformate (0.05 mmol) were added to 23 mg. (0.05 mmol) of the CPZ hapten which was dissolved in 2 ml. of dioxane at 8°C. in an ice-water bath. To eliminate dioxane peroxides, dioxane was treated with basic alumina. To form the mixed anhydride, the reaction was allowed to continue for 20 minutes with occasional stirring. 8 ml. of dioxane was slowly added to 50 mg. of BSA in 10 ml. of water, maintaining the pH of the solution around 9 with 0.1 N NaOH. The mixed anhydride solution was then added dropwise to the BSA solution with constant stirring for 30 minutes at 8°C., maintaining the pH at 9. The solution was stored at 4°C. overnight, then dialyzed for 3 days against dioxane-water (1:1) and for a day against water. After lyophilization, the number of haptenic molecules per BSA molecule was determined as 9 by measuring absorbance at 530 m and comparing with the standard curve of diazotized of CPZ hapten.

EXAMPLE 2

Immunization

New Zealand albino rabbits were immunized with CPZ-BSA conjugate from Example 1 once a week for 3 weeks and then once every 2 to 4 weeks. The immunogen was dissolved in phosphate-buffered saline (pH 7.4) and emulsified with an equal amount of complete Freund's adjuvant. The emulsion containing 500 g. of antigen was injected into the four foot pads (0.1 ml. per foot pad) and 0.6 ml. intramuscularly into both thighs. The booster injection of 1 mg. was given intramuscularly into several sites of the thigh. Bleedings were taken from the central ear artery 6 to 8 days after the third booster immunization. Blood was allowed to clot overnight at 4°C. and then centrifuged at 2,000 rpm. for 15 minutes to separate serum.

EXAMPLE 3

Radioimmunoassay

The antiserum of EXAMPLE 2 as used for the radioimmunoassay was diluted with normal rabbit serum which was diluted with phosphate-buffered saline, pH 7.4, at 1:10 dilution. To determine the antibody titre of antiserum, 0.1 ml. of various dilutions of the antiserum was incubated in an assay tube (10 × 75 mm) with 320 pg of $^3$H-CPZ approximately 7,000 dpm, at 4°C. overnight. The volume was adjusted to 0.5 ml. with phosphate-buffered salie, pH 7.4 which is the optimal pH for the assay. The antibody bound CPZ was separated from free CPZ by the addition of saturated ammonium sulfate which was adjusted to pH 7.4 with ammonium hydroxide as described by Farr, J. Infect. Dis. 103, 239 (1958). After two washings with 50% saturated ammonium sulfate, the precipitate was dissolved in 0.5 ml. of water. The content of the tube was transferred to a counting vial and the tube was then washed four times with 3 ml. of Riaflour. The 12 ml. washings were all collected in the vial. The radioactivity was then counted with a Beckman liquid scintillation counter. Thedilution of the antiserum chosen for further studies were 1:7,000.

Standard curve and specificity

Appropriate volume of phosphate-buffered saline, pH 7.4 was added to all the tubes containing 0.1 ml. of the antiserum to make a final incubation volume of 0.5 ml. To the tubes were added various quantities ranging from 100 ng. to 10 pg. (10 1) of CPZ, its derivatives, serotonin and dopamine. After a 15 minute preincubation, 10 l. of ³H-CPZ was added. The tubes were then incubated overnight at 4°C. followed by precipitation with ammonium sulfate.

A standard curve for plasma was obtained by adding known amounts of CPZ in 10 l. of normal rat plasma to the assay tubes and adjusting the volume to 0.5 ml. with phosphate-buffered saline, pH 7.4.

A standard curve for brain was obtained by adding known amounts of CPZ to a brain homogenate and then extracting by the procedure described below.

A computer program was utilized to obtain the standard curves and values for unknown samples.

Analysis of plasma and brain homogenate

To determine the plasma concentration of CPZ, aliquots of plasma from animals which received CPZ were diluted with normal rat plasma. To the assay tubes containing antiserum, phosphate-buffered saline, pH 7.4, ³H-CPZ and 10 l of unknown samples were added, and incubated at 4°C. overnight. Free CPZ was separated from the antibody bound CPZ by ammonium sulfate precipitation.

Extraction of CPZ from the brain homogenate

The extraction of CPZ from the brain homogenate was necessary as the compound bound to the tissue. The brain was homogenized with 4 volumes of 0.05 N HCl. To a 0.1 ml. aliquot of the brain homogenate, 0.05 ml. of 0.5 N NaOH and 1.5 ml. of petroleum ether containing 10% isopropyl alcohol were added. The tube was vortexed twice for 20 seconds and then centrifuged at 3000 r.p.m. at 8°C. for 10 minutes. The tube was dipped in a dry ice-acetone bath and the aqueous layer was frozen. The upper organic layer was then transferred to another tube and evaporated to dryness under vacuum. The residue was dissolved in an appropriate volume of 25% isopropyl alcohol. To the assay tube containing antiserum, phosphate-buffered saline, pH 7.4 and ³H-CPZ, 10 μl of unknown sample was added. The recovery of CPZ throughout the entire assay range by this extraction procedure was 91.0 ± 0.3% (mean ± S.E.).

Background and non-specific protein binding of ³H-CPZ were determined by excluding the antiserum from the incubation mixture. The counts representing the non-specific binding were then subtracted from all samples.

Procedure on animals

Male Sprague-Dawley rats weighing 210–240 g. were injected intravenously with 10 mg/kg of CPZ hydrochloride. In one group of 6 rats, 0.1 ml. of blood samples were taken from the tail into a heparinized capillary tube at varying time intervals following the injection. The plasma was separated by centrifugation and frozen until assayed. Other 48 rats were killed by decapitation at the same intervals as above, and the brain was removed, frozen on dry ice and then kept in a deep freezer at −80°C. until assayed.

RESULTS

Sensitivity of radioimmunoassay

The antibody in the sera of rabbits immunized with the CPZ-BSA immunogen was determined by the binding of ³H-CPZ. Ouchterlony plates also indicated the presence of the antibody in sera of rabbits immunized with the conjugated CPZ protein. As little as 10 pg. of CPZ can be detected by the antiserum of a rabbit immunized with the CPZ-BSA immunogen. The assay is linear up to 2,000 pg. and identical standard curves can be obtained from plasma and brain as from phosphate-buffered saline, pH 7.4 indicating the lack of interfering substances in these body fluids.

Specificity of radioimmunoassay

The specificity of the antibody in the antiserum of rabbit immunized by the CPZ-BSA immunogen was determined by incubating the antiserum with a number of CPZ derivatives or the biogenic amines in the presence of labeled CPZ. CPZ produced a 50% inhibition of binding of ³H-CPZ to the antibody at a concentration of 118 pg. CPZ substituted at C6, C7, or C8 with hydroxy group was not bound by the antibody to the same extent as CPZ. In order to obtain a 50% inhibition of ³H-CPZ-antibody complex formation, these hydroxylated derivatives of CPZ required concentrations which were 5–10 times that of CPZ. The N-demethylated derivative, $Nor_1$-CPZ was also bound by the antibody to a much lesser extent that CPZ. When both methyl groups were removed, $Nor_2$-CPZ, the antibody failed to recognize the compound unless the concentrations were extremely high. The other major metabolite of CPZ, CPZ-sulfoxide likewise was not recognized by the antibody unless the concentrations were high. The 7hydroxy derivatives of $Nor_1$-CPZ or $Nor_2$CPZ likewise were poorly bound by the antibody. Another metabolic product which can be formed from CPZ is CPZ-N-oxide. This compound is not bound to the antibody to any appreciable extent. Promazine, the dechlorinated derivative required about 8 times the concentration of CPZ to produce a 50% displacement of the labeled CPZ from the antibody.

EXAMPLE 4

Disposition of CPZ in rats

The radioimmunoassay procedure of Example 3 was applied to the determination of CPZ and some minor metabolites in rat plasma and brain following intravenous administration of CPZ hydrochloride.

Following an initial rapid decline, the plasma decay curve indicated a half life of about 4 hours. The brain levels were also plotted against time. Five minutes following the administration of the drug, the brain level of CPZ and metabolites attained a peak level which persisted for 30 minutes, then fell rapidly to give a steady decline curve after 1 hour.

I claim:

1. An antigen consisting essentially of chlorpromazine covalently bonded to an immunogenic carrier material through a diazo containing linking group.

2. The antigen of claim 1 wherein said immunogenic carrier material is bovine serum albumin.

3. The antigen of claim 1 wherein said linking group is diazophenyl carbonyl.

4. The antigen of claim 1 which is chlorpromazine covalently bonded to bovine serum albumin through a diazophenyl carbonyl linking group.

5. An antibody specific to chlorpromazine prepared by innoculating a host animal with an antigen consisting essentially of chlorpromazine covalently bonded to an immunogenic carrier material through a diazo linking group and collecting the serum from said host animal.

6. The antibody of claim 5 wherein said antigen consists essentially of chlorpormazine covalently bonded to bovine serum albumim through a diazophenyl linking group.

7. A method for the assay of chlorpromazine in a sample, which method comprises mixing said sample with a known amount of labeled chlorpromazine compound and an antibody which will selectively complex with said chlorpromazine compound, measuring the degree of binding of said labeled chlorpromazine compound with said antibody, and determining the amount of chlorpromazine present in said sample by comparing said degree of binding to a standard curve obtained by mixing known amounts of chlorpromazine compound with fixed amounts of said labeled chlorpromazine compound and said antibody and determining the degree of binding for each known amount of said chlorpromazine compound.

8. The method of claim 7 wherein radiolabeled chlorpromazine compound is used.

9. The method of claim 8 wherein said radiolabeled chlorpromazine compound is $^3$H-chlorpromazine.

* * * * *